US011179202B2

(12) United States Patent
Hostettler et al.

(10) Patent No.: US 11,179,202 B2
(45) Date of Patent: Nov. 23, 2021

(54) METHOD FOR PLANNING INTRACORPOREAL POSITIONING OF A MEDICAL NEEDLE UNIT TO BE INTRODUCED PERCUTANEOUSLY INTO A PATIENT

(71) Applicant: Medical Templates AG, Egg bei Zuerich (CH)

(72) Inventors: Rafael Hostettler, Munich (DE); Stephan Wetzel, Egg bei Zuerich (CH)

(73) Assignee: MEDICAL TEMPLATES AG, Egg bei Zuerich (CH)

(*) Notice: Subject to any disclaimer, the term of this patent is extended or adjusted under 35 U.S.C. 154(b) by 555 days.

(21) Appl. No.: 16/304,375

(22) PCT Filed: May 8, 2017

(86) PCT No.: PCT/EP2017/060887
§ 371 (c)(1),
(2) Date: Nov. 26, 2018

(87) PCT Pub. No.: WO2017/202590
PCT Pub. Date: Nov. 30, 2017

(65) Prior Publication Data
US 2019/0290362 A1    Sep. 26, 2019

(30) Foreign Application Priority Data

May 25, 2016 (DE) ..................... 10 2016 209 074.7

(51) Int. Cl.
*A61B 34/10* (2016.01)
*A61B 90/11* (2016.01)
(Continued)

(52) U.S. Cl.
CPC .......... *A61B 34/10* (2016.02); *A61B 17/3403* (2013.01); *A61B 90/11* (2016.02);
(Continued)

(58) Field of Classification Search
None
See application file for complete search history.

(56) References Cited

U.S. PATENT DOCUMENTS 5,534,778 A   7/1996 Loos et al.
6,249,713 B1  6/2001 Geiger et al.
(Continued)

FOREIGN PATENT DOCUMENTS

DE          198 05 112 A1    10/1998
DE   10 2011 080 682 A1     2/2013
(Continued)

OTHER PUBLICATIONS

International Search Report for PCT/EP2017/060887, dated Aug. 7, 2017; English translation submitted herewith (7 pgs.).

*Primary Examiner* — Jonathan Cwern
(74) *Attorney, Agent, or Firm* — Fitch, Even, Tabin & Flannery LLP

(57) ABSTRACT

A method is described for planning intracorporeal positioning of a puncture needle to be introduced percutaneously into a patient on the basis of a puncture plan, said method comprising the following steps: a) arranging a needle guide means in a spatially fixed manner on the patient; b) generating and storing a series of cross-sectional images, each containing spatially resolved image information of the patient and of the needle guide means attached in a spatially fixed manner to the patient in a first coordinate system, using an imaging diagnostic method; c) selecting and visually displaying at least one cross-sectional image or a numerically generated cross-sectional image from the series of stored cross-sectional images; d) superimposing a virtual, positionally variable linear trajectory on the basis of the selected cross-sectional image; e) positioning the virtual linear trajectory on the basis of the puncture plan to obtain a target linear trajectory, in which the virtual linear trajectory
(Continued)

a)

b)

traverses the needle guide means; f) numerically determining spatial coordinates of two separate spatial points, or traverse points, within the first coordinate system, at which traverse points the target linear trajectory traverses the needle guide means; g) transforming the spatial coordinates relating to the needle guide means and to the traverse points to a second coordinate system; and h) visually displaying the needle guide means within the second coordinate system in such a manner that the traverse points are shown visibly marked on the needle guide means.

24 Claims, 5 Drawing Sheets

(51) Int. Cl.
    *A61B 17/34*     (2006.01)
    *G01R 33/28*     (2006.01)
    *G16H 30/40*     (2018.01)

(52) U.S. Cl.
    CPC ...... *G01R 33/285* (2013.01); *A61B 2034/107* (2016.02); *G16H 30/40* (2018.01)

(56) References Cited

U.S. PATENT DOCUMENTS

| | | | |
|---|---|---|---|
| 6,366,796 | B1 | 4/2002 | Yanof et al. |
| 6,425,871 | B1 | 7/2002 | Jaggi |
| 6,529,765 | B1* | 3/2003 | Franck ............... A61B 90/10 |
| | | | 600/427 |
| 2002/0183615 | A1 | 12/2002 | Bucholz |
| 2003/0036766 | A1 | 2/2003 | Engelhard et al. |
| 2004/0143150 | A1 | 7/2004 | Barzell et al. |
| 2007/0270687 | A1* | 11/2007 | Gardi ............... G06T 7/254 |
| | | | 600/425 |
| 2008/0146963 | A1 | 6/2008 | Crocker et al. |
| 2010/0298705 | A1* | 11/2010 | Pelissier ............... A61B 8/42 |
| | | | 600/443 |
| 2012/0022358 | A1 | 1/2012 | Fischer |

FOREIGN PATENT DOCUMENTS

| | | |
|---|---|---|
| EP | 0640842 A1 | 3/1995 |
| EP | 2409645 A1 | 1/2012 |
| WO | 92/06645 A1 | 4/1992 |
| WO | 99/058069 A1 | 11/1999 |

* cited by examiner

METHOD FOR PLANNING INTRACORPOREAL POSITIONING OF A MEDICAL NEEDLE UNIT TO BE INTRODUCED PERCUTANEOUSLY INTO A PATIENT

CROSS REFERENCE TO RELATED APPLICATIONS

Reference is made to PCT/EP2017/060887 filed May 8, 2017, and German Application No. 10 2016 209 074.7 filed May 25, 2016, which are incorporated herein by reference in their entirety.

BACKGROUND OF THE INVENTION

Field of the Invention

The invention relates to a method for planning intracorporeal positioning of a medical needle unit to be introduced percutaneously into a patient.

Description of the Prior Art

Several medical situations exist in which a controlled introduction and positioning of a puncture needle at a specific site in the body of a patient is necessary. In particular, biopsy needles for the removal of tissue samples come into use as puncture needles. In addition, also injection needles for the controlled administering of a substance in a specific region in the interior of the body, and guide needles for operation screws or operation drills come into consideration. Puncture needles are also used in the context of medical therapies for targeted stimulation. In all these applications, a defined portion of puncture needle—primarily its tip—is to be positioned at a desired location in the interior of the body. Furthermore, a controlled introduction of the puncture needle is necessary, which is also the entry site on the surface of the body, and the puncture channel are selected on the basis of various criteria.

When a precise as possible introduction and/or positioning of the puncture needle is necessary, the procedure is carried out with the aid of imaging methods. For this purpose, several introduction and positioning devices have already been proposed. Principally, X-ray tomography (CT), fluoroscopy, 3D X-ray, and magnetic resonance tomography (MRT) are used as imaging methods.

EP 0 640 842 A1 describes an MRT assisted biopsy device, which is provided in particular for mammographic investigations. The device comprises a plate, provided with a grid of through-holes, which defines an x-y plane and through which a biopsy needle can be advanced in z-direction. By the choice of a particular through-hole for the needle, a rough x-y positioning is possible. If the x-y position is to be set more precisely than the hole spacing, the entire plate can be displaced continuously in the x-y plane by means of an adjusting device. The device comprises, furthermore, at least one rod-shaped phantom, which is fixed in a known alignment with respect to the housing. The phantom is a material which is visible in the MRT and serves as a positioning aid for the biopsy device. Advantageously, the phantom is configured as an orthogonal cross in which the arms for example run in the x- or respectively y-direction. In one embodiment, in addition, the biopsy needle is equipped in the region of the tip with a further phantom, for determining the z-position of the needle tip is in the MRT image.

The puncture device described in WO 99/058069 which is used for tomography methods is also based on the use of elongated cavities which are filled with a correspondingly selected contrast medium. Given the fact that a plurality of such cavities are present with different direction and offset, the position and inclination of the puncture device can be determined by use of sections of the cavities which are detectable in a tomograph.

EP 2409645 A1 and DE 10 2011 080 682 A1 relate to further imaging-assisted biopsy devices, which comprise a controllable unit for the positioning and the advancing of a biopsy needle. In these cases a positioning unit is used, which permits a controlled needle advance in z-direction and a choice of the needle position in an x-y plane perpendicular thereto. Such an approach is expedient especially in mammographic biopsy devices, because the region of the body which is to be investigated is arranged between two plates and is therefore shaped in a pseudo two-dimensional manner. Accordingly, the access to a particular site is possible advantageously through a puncture transversely to the plane of the plate. Numerous other situations also exist, however, in which a direct puncture on the shortest path perpendicularly to the surface of the skin is not possible, or is at least suboptimal, owing to structures lying in between.

An approach with a selectable puncture angle is described in U.S. Pat. No. 6,249,713. In order to bring the tip of a biopsy needle from a predetermined puncture site to a desired site in the interior of the body, the direction of the needle axis can be adjusted. In particular, this direction can be defined in a manner known per se by a polar angle and an azimuth angle. However, the procedure and also the respective device are comparatively complex.

A further type of biopsy need guidance is described in US published patent application 2008/0146963. This comprises two band-shaped elements connected to one another at their ends, which are each provided with a plurality of through-holes for a biopsy needle. The first band-shaped element is provided for fastening in a fitted manner on a part of a patient's body, wherein the individual through-holes define corresponding puncture positions. The second band-shaped element is longer than the first element between the terminal connections and runs bent upwards accordingly. With a given puncture position, the puncture device can be established approximately by selection of a through-hole in the upper band element. Owing to the flexibility of the upper band element, however, no actual guidance is present, but rather an alignment aid.

The US published patent application 2003/0036766 A1 discloses a needle guide for the intracorporeal placing of a biopsy needle arrangement under visual control by use of a magnetic resonance image monitoring. The needle guide comprises two plates respectively perforated with through-holes with a first plate being positioned close to the body, and a second plate being positioned parallel to and spaced apart from the first. The through-openings within the first and second plates are respectively are dimensioned according to the guiding through the biopsy needle, wherein a specifically selected puncture channel is defined respectively by a through-opening lying in the first and second plate.

In US published patent application 2004/0143150, a comparable needle guide arrangement is described, having a perforated pair of plates which serves for selecting trajectories for an intracorporeal introduction of a medical needle unit. The known needle guide arrangement can be fastened detachably in a stationary manner directly on the patient and in this way represents an extracorporeal, patient-integral needle guide.

The known needle guides, moreover, enable a repeated introduction of the medical needle unit at a specific puncture site along a specifically predetermined puncture channel, as long as the needle guide remains in a fixed connection to the patient.

Although it is possible to carry out the puncture process, that is the introducing of the medical needle unit into the patient, under visual control, that is for example using a method assisted by X-ray image, or similar image, it can occur that the puncture has to be corrected, so that the patient is under stress for at least a second time for the locating of an ideal puncture trajectory. In addition to this, the fact that in particular with the use of visual controls assisted by X-ray image, the doctor is exposed to radiation during the puncture.

From U.S. Pat. No. 6,366,796 a method and a device are described for planning a surgical intervention by way of brachytherapy, in which an operator uses a needle guide which is placed via a stand arrangement relative to a patient, and supported on a plurality of CT tomography images of the patient, which are presented on a display device, together with needle guide, can determine an ideal puncture location and puncture depth before introducing the needle into the patient. This takes place with the aid of a virtual projection needle, which is able to be projected into the CT cross-sectional images, which the operator can position individually through the needle guide depending on patient-specific circumstances. The operator does not receive further assistance for the exact handling of the projection needle. Thus, a great concentration is required of the operator that the projection needle is guided correctly through the needle guide means.

SUMMARY OF THE INVENTION

The invention solves the problem of an attending doctor being able to predetermine and establish an ideal puncture channel for the intracorporeal introduction of the medical needle unit, so that both the stress on the patient can be entirely avoided through avoidance of possible puncture corrections, and also the stress on the doctor due to a radiation exposure can also be entirely avoided. In addition, it is to be ensured that the puncture process can be carried out on the patient reliably and as quickly as possible. For this, the doctor is to be presented with all the information for the intracorporeal introduction of a medical needle unit in an unmistakable and cognitively simply and quick ascertainable manner, in particular for cases in which a needle guide is used which has a large number of needle perforation openings positioned very close together.

According to the invention, a method plans intracorporeal positioning of a medical needle unit to be introduced percutaneously into a patient based on a puncture plan, comprising the method steps:

In a first step, a needle guide is positioned in a spatially fixed manner on the patient over a target region which is securely connected therewith. Preferably, the connection of the needle guide takes place via an adhesive connection, so that the needle guide is able to be positioned to adhesively adhere to the surface of the patient's skin in a gentle manner, and so as to be likewise removable therefrom in a gentle manner for the patient.

In a second step, a series of cross-sectional images, each containing spatially resolved image information of the patient and of the needle guide attached in a spatially fixed manner to the patient is generated and stored according to an imaging diagnostic method. All the image information obtained by use of the imaging diagnostic method is present as spatially resolved image information within a first coordinate system, which is established by the selected system for carrying out the imaging diagnostic method. Likewise, the series of cross-sectional images can be obtained respectively from a three-dimensional image data set, which was obtained from the patient by the needle guide resting on the patient. Basically two, three, four or more suitably selected cross-sectional images can be generated from the set of image data, which are available for further use.

In a next step, at least one cross-sectional image from the series of stored cross-sectional images is selected and displayed visually, preferably on a monitor. Alternatively, it is likewise possible to generate the at least one cross-sectional image numerically on the basis of one or more stored cross-sectional images. The choice of the at least one cross-sectional image is preferably carried out by an attending doctor, whose task is to place the medical needle unit in a specific region inside the patient for the purpose of a specific diagnostic or therapeutic objective.

In a further step, a virtual, positionally variable linear trajectory is superimposed on the selected and displayed cross-sectional image. This process can preferably be carried out using a suitable image processing program, in which the doctor, by manual operation of a graphic input, for example in the form of a computer mouse or a touch-sensitive user input surface, can freely navigate or respectively place a linear trajectory, presented as a line, standing out in a high-contrast manner, with respect to the cross-sectional image displayed on a monitor.

Based on a specifically predetermined puncture plan, the virtual linear trajectory is positioned to obtain a target linear trajectory, in which the virtual linear trajectory traverses the needle guide. The term 'target linear trajectory' is to be understood as the freely selectable, preferably by the doctor, ideal position of a linear trajectory relative to the cross-sectional image displayed on the monitor, along which the medical needle unit is to be introduced intracorporeally into the patient. The target linear trajectory therefore represents the puncture channel for the medical needle unit.

In a subsequent step, the spatial coordinates of two separate spatial points, so-called traverse points, at which the target linear trajectory traverses the needle guide, are determined in the form of spatial coordinates within the first coordinate system.

Subsequently, the spatial coordinates relating to the needle guide and at least the traverse points are transformed from the first into a second coordinate system, within which in a final step the needle guide is visually displayed with the traverse points marked in a visually perceptible manner on the needle guide means.

Within the visual display of the needle guide in which the traverse points stand out as visibly perceptible in high-contrast thereon, the doctor is able to unequivocally detect the exact relative position of the target linear trajectory of the needle guide, so that based of this information, which is conveyed to the doctor visually, the doctor can introduce the medical needle unit into the patient in an unerring manner quickly via the needle guide, attached securely to the patient, at the predetermined position and following the predetermined puncture channel direction.

All the provisions which are to be taken into consideration for locating or respectively determining the target linear trajectory, such as for example the location of a freely accessible puncture channel through the surface of the skin to a specific intracorporeal region, without touching or respectively injuring intracorporeal objects, such as for example organs, vessels, bones, etc., can be carried out by the doctor separately from the patient, calmly and carefully, at a computer-assisted, image-processing workstation. Neither the patient nor the respective doctor are exposed to stresses such as for example in the form of adjustment punctures or radiation exposures.

In order to facilitate the locating of the target linear trajectory for the doctor, a preferred further development of the method according to the invention display at least two cross-sectional images simultaneously in a visually perceptible manner is provided, which respectively depict a patient view and the needle guide from different viewing angles. In both cross-sectional image presentations, the linear trajectory, which is freely movable manually by the doctor, is brought respectively into superimposing presentation, by use of which it is possible for the doctor to obtain a three-dimensional impression regarding the location of the virtually displayed linear trajectory relative to the spatial conditions of the patient in a manner which is cognitiviely easy for the doctor to ascertain. The two or more cross-sectional images, which are displayed respectively immediately adjacent to one another, can be illustrated on different monitors or in cross-sectional image areas displayed separately on one monitor. The type, size and graphic display form of the respective cross-sectional images through the patient and the needle guide arranged securely thereon and the linear trajectory brought respectively into superimposition with the cross-sectional images is to be selected in an optimized manner subject to a way which is able to be ascertained cognitively by the doctor reliably, unequivocally and quickly.

As the further embodiments will show in particular with reference to a practical example embodiment, the situation preferably presents itself to arrange a needle guide in a detachably secure manner onto the patient, which comprises at least an upper plate element positioned remote from the patient and a lower plate element positioned facing the patient, which are respectively spaced rigidly with one another and from one another and respectively provide a plurality of through-holes for the guiding through of a medical needle unit.

The process of positioning the virtual linear trajectory takes place based on the specific puncture plan, which comprises at least the number of medical needle units to be introduced intracorporeally and their intracorporeal position and location, in particular respectively of the distal needle tip, and ultimately leads to obtaining the ideal target linear trajectory for respectively one medical needle unit, wherein the target linear trajectory runs respectively through a through-hole of the upper and lower plate element. Of course, two or more medical needle units can also be introduced simultaneously into the patient via a needle guide. For establishing the target linear trajectories associated with the individual medical needle units, in addition it is taken into account that they do not penetrate one another spatially.

The graphic display of the needle guide on a cross-sectional image takes place in the simplest case through the spatially resolved image information obtained within the imaging diagnostic method. In a preferred method variant, the needle guide is represented based on the CAD data set known per se, which represents the exact spatial shape of the needle guide, numerically generated and brought in to superimposition true to size and spatial angle to the cross-sectional image representation. For this, a marker, arranged in a spatially fixed manner at the needle guide is presented in as high-contrast a manner as possible in the generated and stored cross-sectional images, which is detected using a numerical pattern recognition program in a positionally resolved manner within the first coordinate system. Based on the locationally resolved marker, spatially resolved image data of the needle guide are generated synthetically and are superimposed graphically on the cross-sectional image. In this way, a highly accurate spatially resolved representation, true to size and spatial angle, of the needle guide is generated on the respectively visually displayed cross-sectional images.

On the basis of the image data visually reproducing the needle guide and the spatial coordinates determining the target linear trajectory, the spatial coordinates of the traverse points, at which the target linear trajectory traverses the needle guide, are determined by use of a suitable image evaluation program. In the case of the use of the needle guide already explained above, comprising at least the upper and lower plate element, the traverse points characterize the through-holes within the upper and lower plate element through which the target linear trajectory projects.

The goal is to convey to the doctor the information required to introduce an actual medical needle unit into the needle guide actually arranged in a spatially fixed manner on the patient, so that the medical needle unit is guided through the actual needle guide in precisely the same spatial orientation and location for the purpose of patient puncture, in which the virtually displayed target linear trajectory traverses the virtual needle guide reproduced on the screen.

In order to convey this information to the doctor in an easily cognitively accessible and error-free manner, the needle guide displayed on the respective cross-sectional image, together with the target linear trajectory traversing the latter, is reproduced in a separate representation. For this, it is necessary to transform the spatial coordinates of all image data of the needle guide and at least the spatial coordinates of the two traverse points from the first into a second coordinate system. Alternatively, the possibility exists, instead of the transformation of the spatial coordinates of all image data representing the needle guide, to only transform the spatial coordinates of the detected at least one marker of the needle guide into the second coordinate system. For a whole virtual representation of the needle guide within the second coordinate system, recourse is made to the known data, preferably in the form of CAD data, describing the spatial form of the needle guide. Hereby, the necessary computing time for the transformation can be reduced, whereby computing times can be shortened and, if applicable, computing capacities can be cut down. The intent and purpose of the coordinate transformation into the second coordinate system is a separate representation of the needle guide with the two traverse points. Through a suitable virtual presentation, the doctor can study the precise site of the traverse points. For example, it is possible to spatially rotate the needle guide together with traverse points in a three-dimensional representation through a correspondingly user-specific input, in order to easily detect the traverse points.

Preferably, the visual representation of the needle guide with the traverse points, marked in a visually perceptible manner at the needle guide, is carried out within the second coordinate system in such a way so that in the case of a needle guide of the type designated above, the upper and lower plate element are reproduced separately, respectively in top view, wherein on the plate elements respectively data unequivocally locating the through-holes are represented visually. In a preferred embodiment, the through-holes are divided into rows and columns, so that an unequivocal through-hole specification can be carried out by a specific pair of values. Preferably, alphanumeric characters are suitable for this, for the designation of the through-holes distributed along a column and a line. Of course, alternative designations are also conceivable for the specification of the individual traverse points.

In the knowledge of this information, specifying the through-holes, the doctor can guide the actual medical needle unit through the actual needle guide.

The method according to the invention makes possible, by use of the detection of the at least one marker arranged at the needle use means, a verification of the needle guide which is used, by the detected marker being compared with reference marker data stored accordingly in a data bank or respectively a library. On coincidence, the actually used needle guide is detected and can be assigned to a data set for describing the entire spatial shape of the needle guide which is concerned. Such a data comparison makes possible the detection of possible plagiarisms within the verification. Furthermore, the data comparison makes possible an automatic allocation of the respectively used needle guide means to a specific category of needle guide which differ from one another for example respectively in shape and size.

BRIEF DESCRIPTION OF THE DRAWINGS

The invention is described by way of example below, without restriction of the invention, by description of example embodiments with reference to the drawings. There are shown:

FIG. 1 *b* is a top view onto the upper plate element of the needle guide;

FIG. 1 *c* is a top view onto the lower plate element with support structures of the needle guide;

DETAILED DESCRIPTION OF THE INVENTION

Figure 1A:
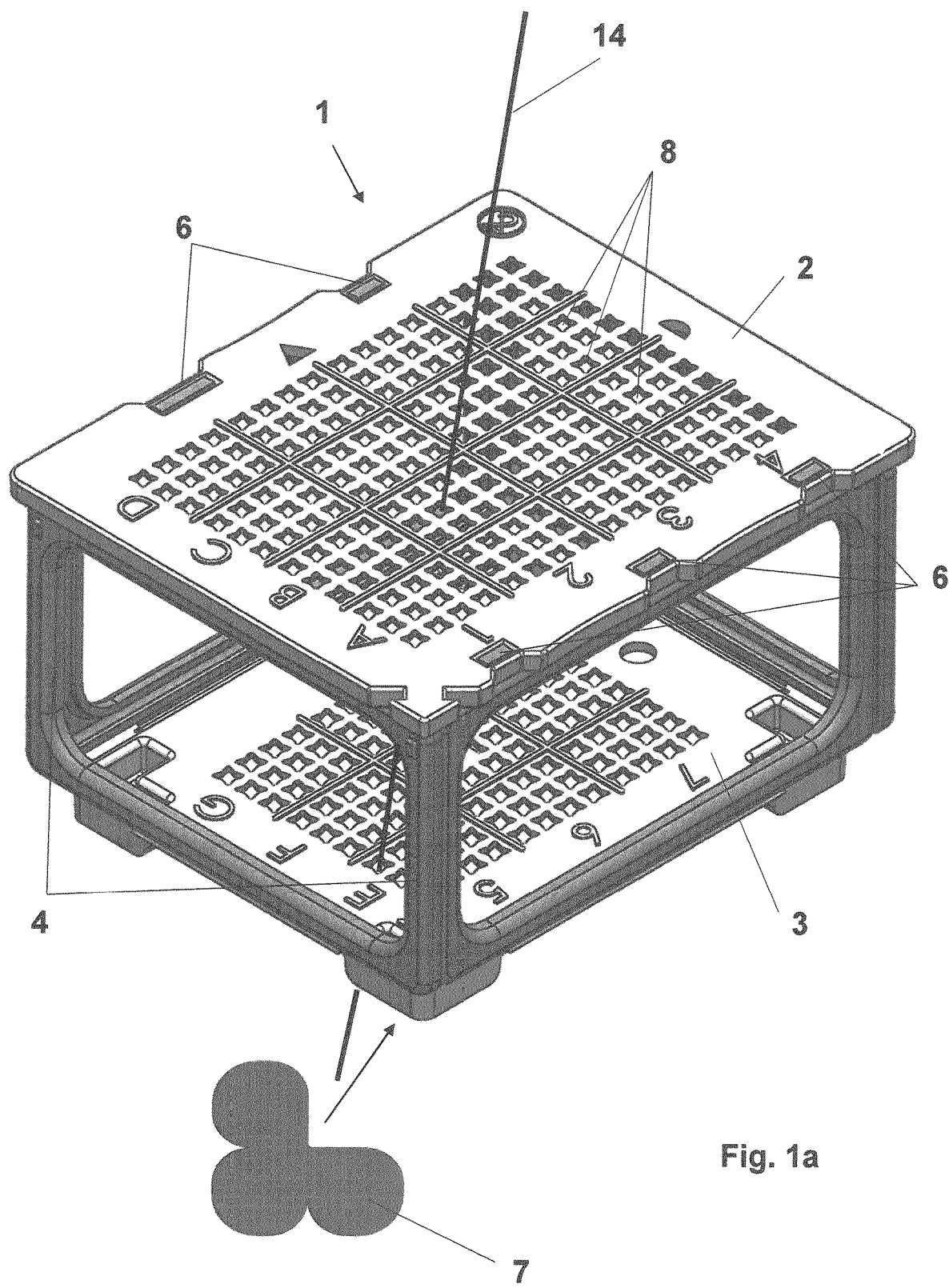
FIG. 1 *a* is an overall illustration of a preferred needle guide.
Figure 1B:
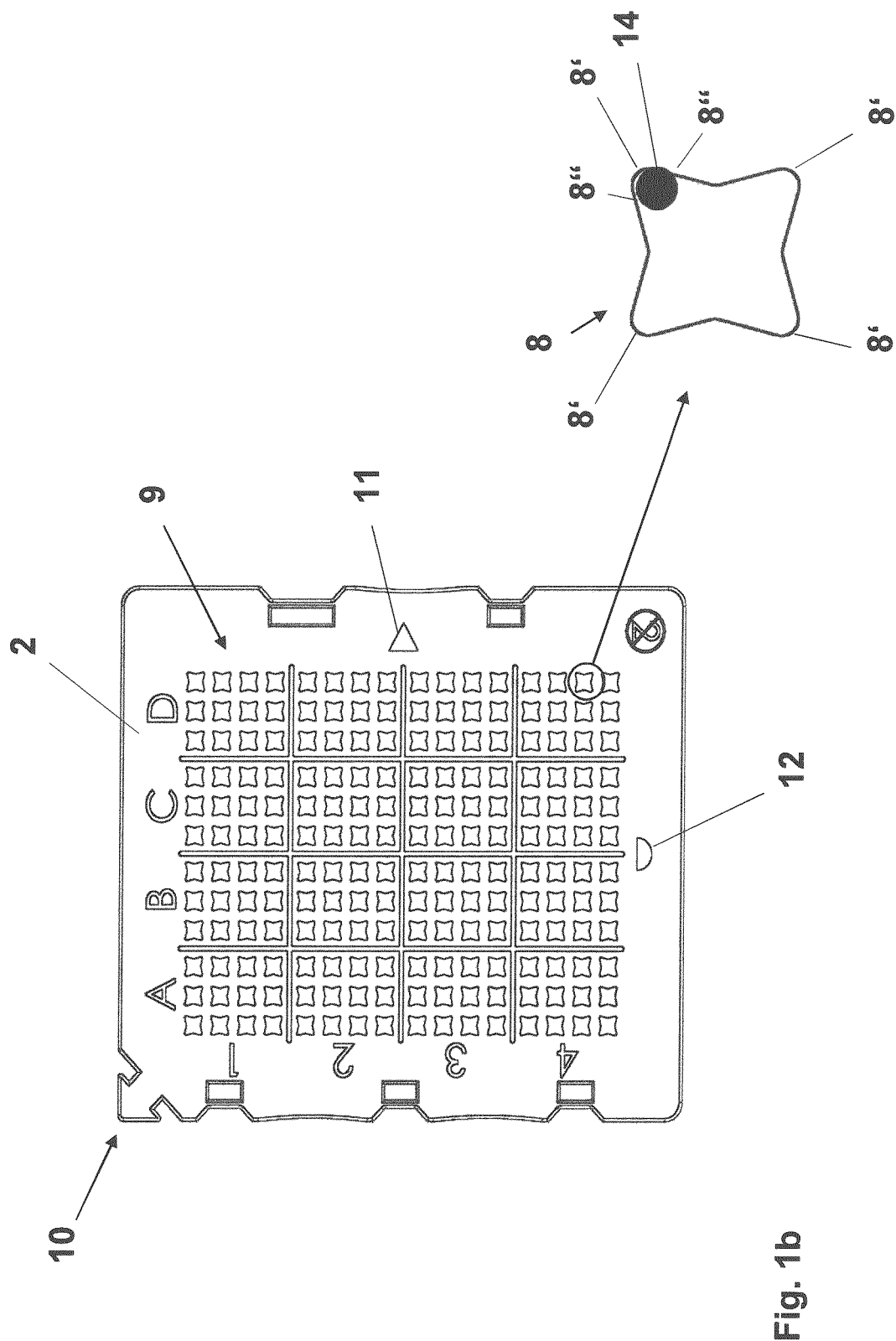
Figure 1C:
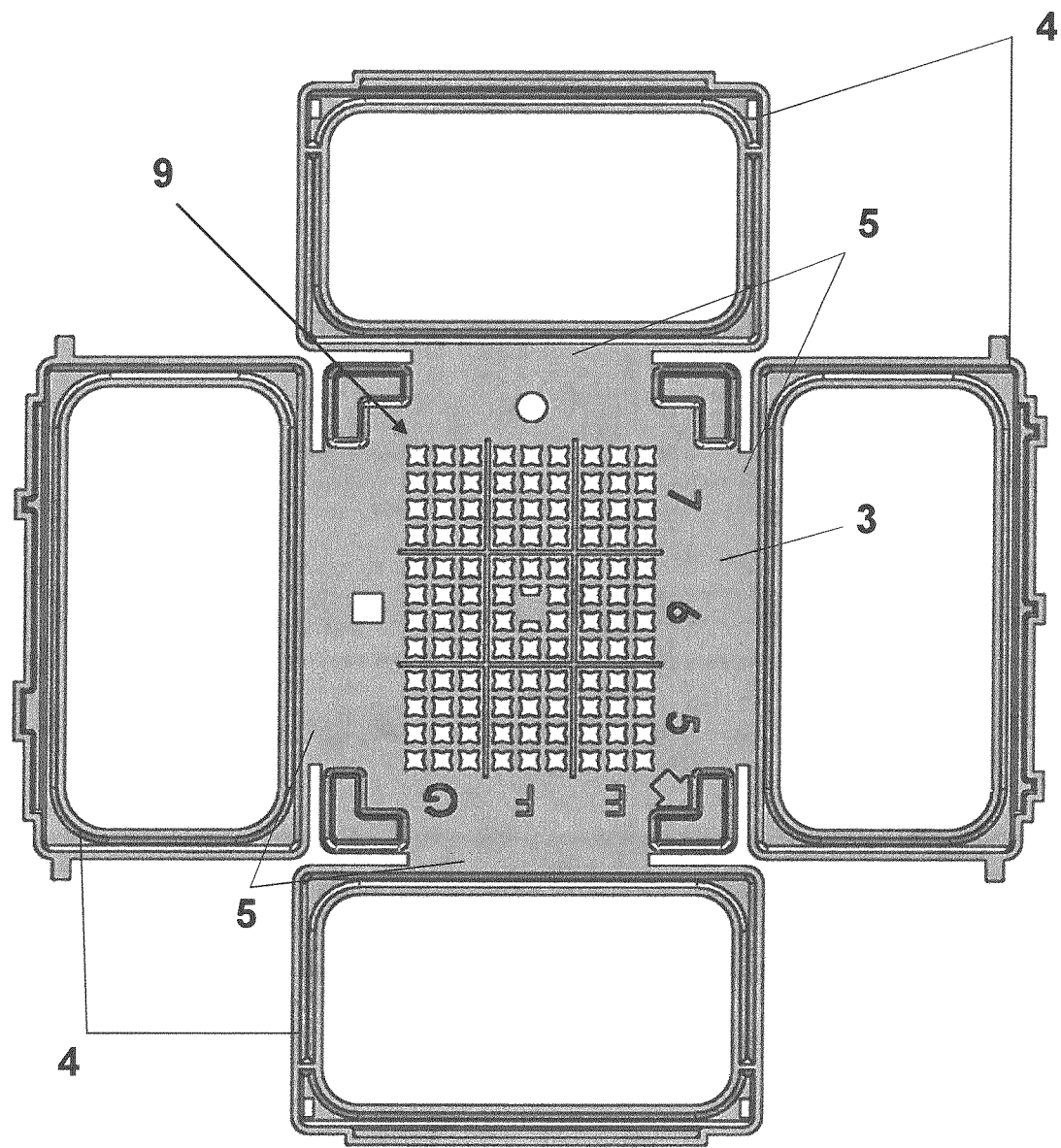

In FIG. 1*a* a preferred needle guide 1 is illustrated overall perspectively. The needle guide has an upper plate element 2 and a lower plate element 3, which are both mounted parallel to one another and are arranged spaced apart from one other laterally via a support structure 4. In FIG. 1*b* the upper plate element 2 is illustrated in a top view and in FIG. 1*c* the lower plate element 3 is likewise illustrated in a top view with the support structures 4 articulated thereon. For further description relating to the needle guide 1, reference is to be made to FIGS. 1*a* to 1*c* jointly.

The needle guide 1 illustrated in FIG. 1*a* is made from a biocompatible material, preferably from a sterilizable plastic material, which permits use in sterile spaces with direct patient contact. Preferably, the needle guide 1 is manufactured by way of a primary shaping method or generative production method. The needle guide 1 has an upper plate element 2 and a lower plate element 3. Both plate elements 2, 3 are spaced apart via a support structure 4 which is connected in one piece with the lower plate element 3. The support structure 4 is preferably pivotably connected via hinge joints 5 with the lower plate element 3 articulatedly respectively about an axis. Both plate elements 2, 3 are securely connected in a detachable manner via suitably constructed detent connections 6 and constitute, in the joined-together state, a parallelepiped- or cube-shaped basic shape. The detent connections 6 are configured and arranged such that a joining together of both plate elements 2, 3 is possible only in a single unequivocal association.

For purposes of a securing of the needle guide means 1 in a spatially fixed manner on the surface of a patient's skin (not illustrated), suitably configured adhesions 7 are provided on the lower plate element 3 which in the form of adhesive pads produce a temporary adhesive connection with the patient's skin. The shape of the adhesive pads 7 is preferably selected such that they are able to be applied, as far as possible free of folds, on different contours of the body. PVC foam which is coated on one side with a biocompatible adhesive for application on the skin is preferably suitable as material.

The main function of the needle guide 1 is to spatially determine the position and location of a medical needle unit 14 which is introduced intracorporeally into a patient through the skin. For this, the needle guide 1, adhering in a spatially fixed manner on a patient, serves to be guided through the one medical needle unit 14 for the purposes of patient puncture. Here, the needle unit 14 penetrates both the upper and also the lower plate element 2, 3, which respectively have a plurality of through-openings 8 arranged in an ordered manner. In the example embodiment, the upper plate element 2 has 144 through-openings 8 and the lower plate element 3 has 82 through-openings 8. The through-openings per plate element lie very closely adjacent to one another. Typically, the reciprocal distance of the opening mid-points of two adjacent through-openings is approximately 2 mm to 7 mm. Therefore, the spatial location of the needle unit 14 can be characterized by two through-openings, namely by a through-opening within the upper plate element 2 and by a through-opening within the lower plate element 3, through which respectively the medical needle unit projects.

The method according to the invention, which is described hereinafter, serves the respective user, preferably a doctor, for the exact cognitive detection of the two through-openings, through which the medical needle unit passes. Suitably configured markings and labels serve in particular for this, which are arranged both on the upper and also on the lower plate element 2, 3.

Each of the two plate elements 2, 3 has a plurality of suitably configured through-openings 8, which respectively enable a guiding through of the medical needle unit 14 through the needle guide 1 and, moreover, ensure a reliable guiding and positioning of the needle unit 14 within the needle guide. In the example embodiment which is shown, the shape of the through-openings 8 is configured so as to be star-shaped and offers four support site regions 8' for the medical needle unit 14, shown in detail in the illustration in FIG. 1*b*. The geometry is selected so that a medical needle unit 14 is always guided by two flanks 8" lying opposite one another and is centered within the respective support site region 8'. In this way, an inadvertent slipping of the medical needle unit 14 within a through-opening 8 is prevented to the greatest possible extent. In addition, the risk is reduced that the medical needle unit 14 comes to rest against a different support site region 8' within the through-opening 8. Of course, alternative geometries are conceivable for the configuration of the through-openings. In order to increase the number of possible support site regions 8' within a through-opening 8, more than for placing possibilities can be provided for the medical needle unit, by the number of star-shaped corners being increased, for example.

The individual through-openings 8 are integrated both in the upper plate element 2 and also in the lower plate element 3 respectively to fields 9, whereby a better orientation and retrieval of an individual through-opening 8 becomes possible. Each field 9 has twelve through-openings 8 and therefore contains a total of 48 different support site regions 8'. The through-openings 8 are arranged within a field 9 respectively in three columns and four rows, whereby the field 9 receives a spatial orientation. In this way, the doctor can simply identify more easily a through-opening 8 within a field 9 based on the spatial orientation. The identification of a specific support site region 8' also becomes possible more easily through the field arrangement of the through-openings.

The upper plate element has sixteen fields 9, which have respectively geometrically and in a visually perceptible manner a lateral distance from one another. The sixteen fields 9 are therefore arranged in four rows and four columns. In total, the upper plate element 3 has 768 support site regions 8'.

By comparison, the lower plate element 3 has only nine fields 9, which are arranged respectively in three rows and three columns. Therefore, the lower plate element 3 has only 428 support site regions 8'.

For the purposes of an easy and unequivocal field allocation, the fields 9, arranged in columns and rows, are marked with alphanumeric characters. Thus, each field column is designated by a letter (A to D with respect to the upper plate element 2 and E to G with respect to the lower plate element 3) and each field line is designated by a number (1 to 4 with respect to the upper plate element 2 and 5 to 7 with respect to the lower plate element 3). The alphanumeric markings are respectively stamped onto the surface of the two plate elements 2, 3, so that they are clearly prominent visually. A specific field 9 is consequently unequivocally identified by a combination of the letters of the respective column and number of the respective line.

In addition, at least the upper plate element 2 has a marking 10, which is configured in the form of an arrow. The marking 10 permits an unequivocal identification of the spatial orientation of the upper plate element 2. The marking 10 is a uniquely occurring feature, whereby the determining of the orientation is unequivocal. The marking 10 is arranged in a corner of the upper plate element 2 and is therefore clearly prominent visually.

Through an asymmetrical configuration and arrangement of the detent connections 6 between the upper plate element 2 and the lower plate element 3, a distorted and incorrect arrangement of both plate elements 2, 3 relative to one another can be reliably ruled out. In this respect, the spatial detection of the marking 10 also serves for determining the spatial arrangement and alignment of the entire needle guide 1.

In addition, the upper plate element 2 has further markings 11, 12, which owing to their triangular or respectively semi-circular shape can be located and detected by use of numerical pattern recognition within an image data evaluation. The markings 11, 12 serve both for an automatic location and orientation detection of the needle guide 1 within an image evaluation method. They also serve additionally, however, as visual reference points for a doctor, for easier, more reliable and quicker detection of a specific through-opening 9 on the upper plate element.

Hereinafter, the use of the needle guide 1, explained above, is assumed, which in the above configuration is securely arranged on the surface of a patient's skin. The patient is subjected to an imaging diagnostic method, for example an NMR or CT method, which delivers cross-sectional images through the patient and also through the needle guide 1.

Figure 2A:
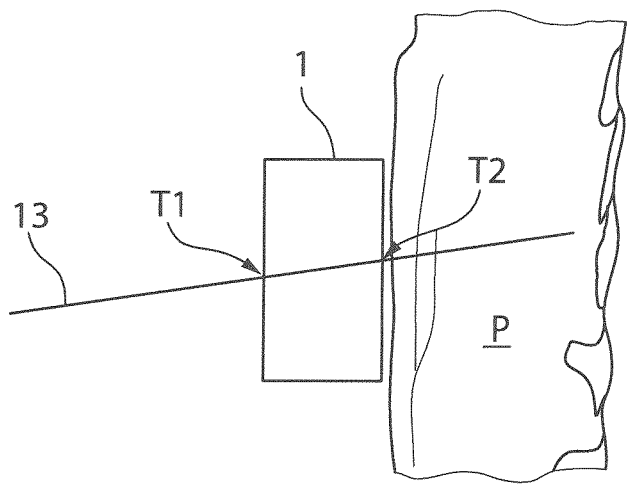
FIG. 2 *a, b* are NMR cross-sectional images through a patient with the needle guide means and superimposed linear trajectory.
Figure 2B:
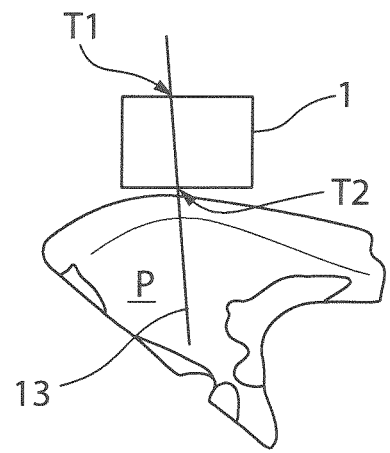

In FIG. 2 *a* and *b*, typical CT image recordings in the form of cross-sectional image presentations are shown, which showed both a cross-sectional image through the patient P and also a cross-sectional image through the needle guide 1 resting on the patient P, and reproduce the patient and the needle guide at a different viewing angle. By use of the two different viewing angles onto one and the same intracorporeal region within the patient P, the doctor is able to have a three-dimensional view of the situation which is being observed. The cross-sectional images presented respectively adjacent to one another on a monitor make possible for the doctor, moreover, a superimposing of the cross-sectional images with a freely positionable linear trajectory 13. The spatial alignment of the trajectory relative to the patient P is variable as desired by the doctor by use of a suitable input, for example by use of a computer mouse. The linear trajectory 13, standing out in a high-contrast manner over the presented cross-sectional images can be placed by the doctor so that only a minimal stress occurs for the patient P during a subsequent puncture. During locating of an ideal puncture channel, which corresponds to a so-called target linear trajectory 13, the target trajectory 13 passes through the needle guide means 8, likewise presented in the cross-sectional images; which is the case in the images according to FIG. 2*a*, *b*. By use of the presented cross-sectional images, the doctor cannot, however, see through which through-openings 8 the target linear trajectory 13 passes respectively within the upper and lower plate element 2, 3.

For the purposes of the precise identification of the traverse points T1, T2 of the target linear trajectory 13 through the needle guide 1, first a numerical determining of the spatial coordinates of the two traverse points T1, T2 takes place within the first coordinate system established on the part of the imaging recording technology, within which all image data is present in a spatially resolved manner. However, in order to convey to the doctor the information as to through which through-openings 8 the target linear trajectory 13 passes respectively along the upper and lower plate element 2, 3, and in particular at which support site regions 8' the medical needle unit 14 is to come to rest, the traverse points T1, T2 and the representation of the needle guide 1 is to be transformed into a second coordinate system.

Figure 3:
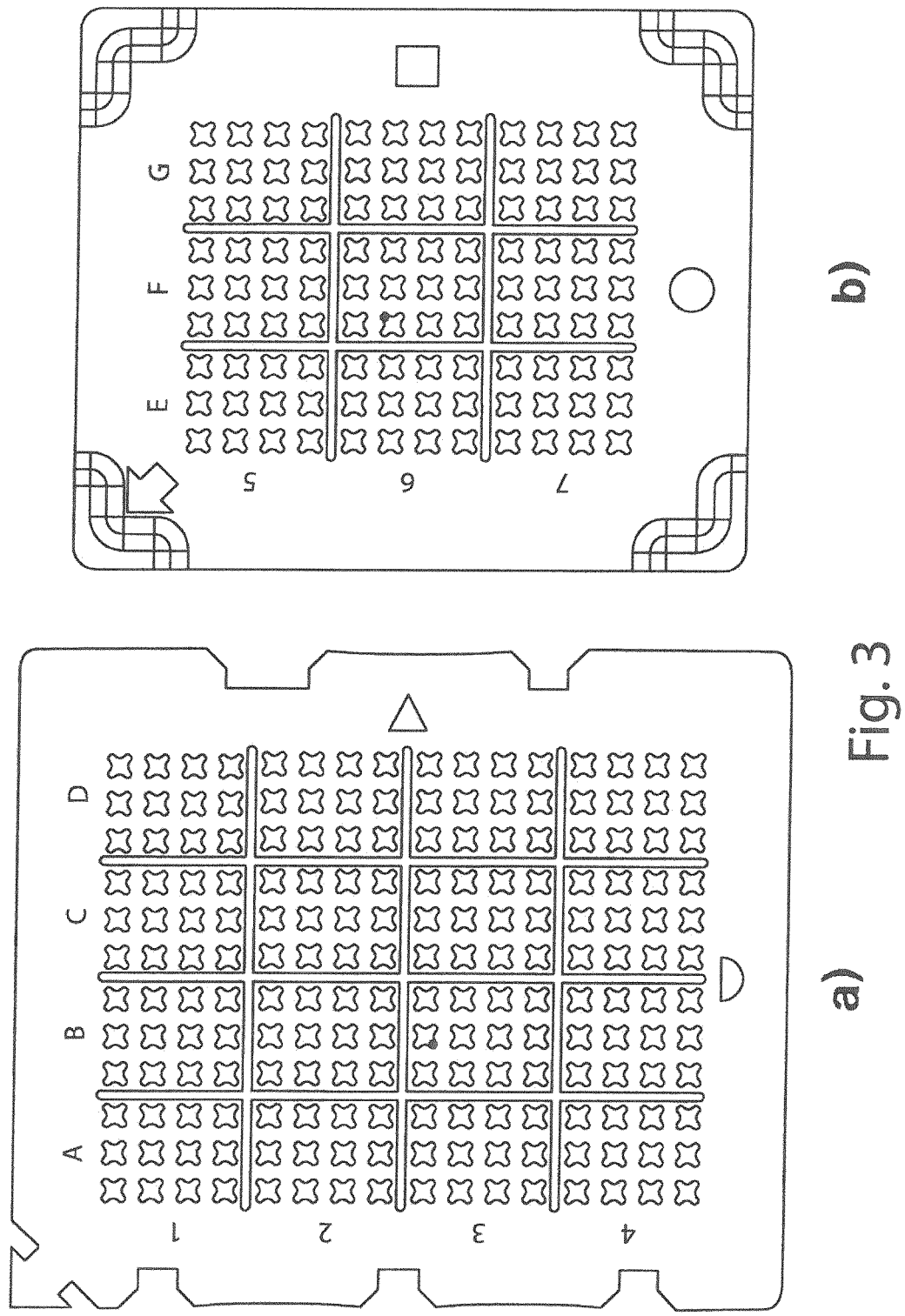
FIG. 3 *a, b* are top view illustrations of the upper and lower plate element with traverse points

For visual display, the needle guide is preferably presented in two cross-sectional images lying adjacent to one another. FIG. 3*a* shows the top view onto the upper plate element 2 and FIG. 3*b* shows the top view onto the lower plate element 3. In both plate elements respectively, the penetration point or respectively the traverse point T1, T1 is highlighted in a high-contrast manner. In the illustrated case, the target linear trajectory traverses the upper plate element 2 through a through-opening 8 which lies in the field B3 and there in the through-opening topmost line, middle column. The support site region 8' is situated bottom left within the through opening. In the case of the lower plate element 3, the traverse point is situated in the field F6 and here in the through-opening second line, right column. The support site region in this through-opening is top right.

The above description for a quick and reliable, that is an error-free detection of the traverse points for the doctor is based on a three-stage description concept. In one step, one traverse point per plate element is characterized by the indication of in which field 9 the traverse point lies. This characterisation takes place through a letter/number combination, B3 for the upper plate element and F6 for the lower plate element. Any confusion between the two plate elements is ruled out in addition because the letters and numbers per plate element are not repeated.

In a second step, the respective traverse point is characterized within the respective field 9. In the upper plate element, the traverse point is situated within the field 9 in the first line, second column, i.e. abbreviated to (Z1, S2); in the lower plate element, the traverse point is situated within the respective field 9 in the second line, first column i.e. abbreviated to (Z2, S1).

In the third step, the traverse point is characterized by the support site region 8' within the respective through-opening 8. In the upper plate element, the traverse point is situated within the through-opening 8 in the lower left corner, i.e. abbreviated to "bottom left"; in the lower plate element, the traverse point is situated within the respective through-opening 8 in the upper right corner, i.e. abbreviated to "top right".

Therefore, for the precise location description of both traverse points, the following coordinate descriptions result: (B3/Z1,S2/bottom left; F6/Z2,S1/top right). In a preferred form, these coordinate designations are displayed visually on a monitor and/or are implemented so as to be perceived acoustically.

The entire image data processing takes place in such a way so that the presentations according to FIGS. 2*a, b* and FIGS. 3*a*, 3*b* are brought simultaneously to view for the doctor, so that the doctor, on locating of the target linear trajectory, can always assess whether the target linear trajectory in fact also passes through respectively a through-opening within the upper and lower plate element. If the linear trajectory, presented in a high-contrast manner, lies outside the respective through-openings, then the doctor must readjust accordingly.

LIST OF REFERENCE NUMBERS

1 needle guide
2 upper plate
3 lower plate
4 support structure
5 film hinge joint
6 detent
7 adhesion
8 through-opening
8' support site region
8" flanks
9 field
10 marking
11 marking
12 marking
13 linear trajectory, target linear trajectory
14 medical needle
P patient
T1, T2 traverse points

The invention claimed is:

1. A method for planning intracorporeal positioning of a puncture needle to be percutaneously introduced into a patient based on a puncture plan comprising:
   a) positioning a needle guide in a spatially resolved manner on the patient through which the puncture needle passes;
   b) using an imaging diagnostic method to generate and store a series of cross-sectional images with each cross-sectional image containing spatially resolved image information of the patient and of the needle guide attached in a spatially resolved manner on the patient in a first coordinate system;
   c) selecting and visually displaying at least one cross-sectional image or at least one generated cross-sectional image from the stored cross-sectional images;
   d) superimposing a virtual positionally variable linear trajectory on the at least one selected cross sectional image based on the selected at least one cross sectional image;
   e) positioning the virtual positionally variable linear trajectory to obtain a target linear trajectory through which the needle guide passes which represents a puncture channel of the puncture needle to pass through the patient;
   f) determining spatial coordinates of two separately resolved traverse points within the first coordinate system at which the two separate traverse points traverse the needle guide;
   g) transforming spatial coordinates relating to the needle guide and to the two separate spatial traverse points into a second coordinate system; and
   h) visually displaying the needle guide within the second coordinate system to visually mark the two separate traverse points to be visually perceptible on the needle guide.

2. The method according to claim 1, wherein in step h):
two cross-sectional images are displayed simultaneously to be perceptible visually to show the virtual linear trajectory and the patient together with the needle guide from different viewing angles.

3. The method according to claim 2, wherein in step h):
the visual display of the needle guide within the second coordinate system presents each traverse point in a separate cross-sectional image through the needle guide.

4. The method according to claim 3, comprising:
generating spatially resolved image information from the needle guide fixedly attached to the patient by using numerical pattern recognition of at least one marker positioned at the needle guide with the spatial position and location thereof being determined within the first coordinate system.

5. The method according to claim 4, comprising:
using data describing a spatial shape of the needle guide and based on a position and location of the at least one marker within the first coordinate system, generating spatially resolved image data of the needle guide.

6. The method according to claim 2, comprising:
generating spatially resolved image information from the needle guide fixedly attached to the patient by using numerical pattern recognition of at least one marker positioned at the needle guide with the spatial position and location thereof being determined within the first coordinate system.

7. The method according to claim 6, comprising:
using data describing a spatial shape of the needle guide and based on a position and location of the at least one marker within the first coordinate system, generating spatially resolved image data of the needle guide.

8. The method according to claim 2, comprising:
calculating at least one, visually displayed, numerically generated cross-sectional image based on a selection of cross-sectional images obtained from the imaging diagnostic method.

9. The method according to claim 1, wherein in step h):
the visual display of the needle guide within the second coordinate system presents each traverse point in a separate cross-sectional image through the needle guide.

10. The method according to claim 9, comprising:
generating spatially resolved image information from the needle guide fixedly attached to the patient by using numerical pattern recognition of at least one marker positioned at the needle guide with the spatial position and location thereof being determined within the first coordinate system.

11. The method according to claim 10, comprising:
using data describing a spatial shape of the needle guide and based on a position and location of the at least one marker within the first coordinate system, generating spatially resolved image data of the needle guide.

12. The method according to claim 9, comprising:
calculating at least one, visually displayed, numerically generated cross-sectional image based on a selection of cross-sectional images obtained from the imaging diagnostic method.

13. The method according to claim 1, comprising:
generating spatially resolved image information from the needle guide fixedly attached to the patient by using numerical pattern recognition of at least one marker positioned at the needle guide with the spatial position and location thereof being determined within the first coordinate system.

14. The method according to claim 13, comprising:
using data describing a spatial shape of the needle guide and based on a position and location of the at least one marker within the first coordinate system, generating spatially resolved image data of the needle guide.

15. The method according to claim 14, comprising:
detecting the at least one marker positioned at the needle guide numerically and locating spatial coordinates thereof in the first coordinate system, and based on located spatial coordinates of the at least one marker, transforming the image data of the needle guide, and transforming spatial coordinates of two traverse points into the second coordinate system.

16. The method according to claim 14, comprising:
calculating at least one, visually displayed, numerically generated cross-sectional image based on a selection of cross-sectional images obtained from the imaging diagnostic method.

17. The method according to claim 13, comprising:
detecting the at least one marker positioned at the needle guide numerically and locating spatial coordinates thereof in the first coordinate system, and based on located spatial coordinates of the at least one marker, transforming the image data of the needle guide, and transforming spatial coordinates of two traverse points into the second coordinate system.

18. The method according to claim 17, wherein:
at least one, visually displayed, numerically generated cross-sectional image is calculated based on a selection of cross-sectional images taken by use of the imaging diagnostic method.

19. The method according to claim 13, comprising:
calculating at least one, visually displayed, numerically generated cross-sectional image based on a selection of cross-sectional images obtained from the imaging diagnostic method.

20. The method according to claim 1, comprising:
calculating at least one, visually displayed, numerically generated cross-sectional image based on a selection of cross-sectional images obtained from the imaging diagnostic method.

21. The method according to claim 1, comprising:
after obtaining the target linear trajectory, determining spatial coordinates of the two traverse points through the needle guide based on known image information of the needle guide within the first coordinate system.

22. The method according to claim 1, wherein:
the needle guide comprises at least an upper plate element, located away from the patient, and a lower plate element, located facing the patient, which are rigidly spaced apart and respectively provide through-holes for the puncture needle to be guided; and comprising:
positioning a virtual linear trajectory based on the puncture plan for obtaining a linear trajectory which runs respectively through a hole of the upper plate element and a hole of the lower plate element.

23. The method according to claim 22, wherein:
the visual display of the needle guide has traverse points marked on the needle guide which are visually perceptible and are located within the second coordinate system so that upper and lower plate elements are reproduced separately in a top view and wherein on the plate elements data locates the through-holes.

24. The method according to claim 23, wherein:
the data locating the hole penetrated by the target linear trajectory in the upper and lower plate element is indicated in alphanumeric form.

* * * * *